United States Patent [19]

Masuda et al.

[11] Patent Number: 4,917,799
[45] Date of Patent: Apr. 17, 1990

[54] FILTERING DEVICE FOR BLOOD PLATELETS

[75] Inventors: Kazuhiko Masuda, Takatsuki; Masami Ohnishi, Osaka, both of Japan

[73] Assignee: Nissho Corporation, Osaka, Japan

[21] Appl. No.: 263,757

[22] Filed: Oct. 28, 1988

[30] Foreign Application Priority Data

Nov. 5, 1987 [JP] Japan .................. 62-279985

[51] Int. Cl.$^4$ ............................................. B01D 39/04
[52] U.S. Cl. .................................. 210/435; 210/496; 210/508
[58] Field of Search ............... 210/496, 503, 505, 508, 210/435, 446

[56] References Cited

FOREIGN PATENT DOCUMENTS 0155003 9/1985 .

*Primary Examiner*—W. Gary Jones
*Attorney, Agent, or Firm*—Armstrong, Nikaido, Marmelstein, Kubovcik & Murray

[57] ABSTRACT

A filtering device for blood platelets comprises polyester fibers having an average cross-sectional diameter of 0.1 to 5 μm, wherein there is formed electro-microscopic roughness on the surface of the polyester fibers. According to the present invention, there can be realized a filtering device for blood platelets having simple construction, wherein blood platelets are caught efficiently and the removal of blood platelets is carried out in a short time.

3 Claims, 6 Drawing Sheets

FILTERING DEVICE FOR BLOOD PLATELETS

BACKGROUND OF THE INVENTION

The present invention relates to a filtering device for blood platelets, and more particularly to a filtering device separating blood platelets from blood and/or body fluids.

There occurs adhesion and coagulation when blood platelets are contacted with any surface other than that of blood vessels due to coagulation ability thereof, and therefore, there is a problem that tissue death occurs during an operation for human body due to obturation formed by coagulated blood platelets.

Accordingly, in order to avoid unnecessary bleeding, blood platelets are removed from human body before performing operation, and then blood platelets are transfused into human body after the operation.

As a means suitable for catching such blood platelets, National Publication of Translation of International Application No. 502174/1987 discloses a device wherein blood is poured into an ultrafilter comprising hollow fibers in order to catch blood platelets and store concentrated blood platelets.

Further, Japanese Examined Patent Publication No. 54125/1983 discloses a leukocyte filtering device, wherein fibers hvaing an average diameter of under 10 μm are packed into a column so that mass of fibers is characterised as possessing a bulk density of under 0.15 g/cm³.

However, the device, which catches blood platelets by the ultrafilter, as shown in National Publication of Translation of International Application No. 502174/1987, has a disadvantage that it cannot treat enough blood since coagulation of blood platelets occurs inside of the hollow fiber.

And also, the filtering device, wherein fibers are packed into a column, as shown in Japanese Examined Patent Publication No. 54125/1983, has a disadvantage that separating effeciency is low since blood platelet absorbing ratio is low.

Further, unless a bulk density is suitably selected, filtered blood tends to contain hemolysis component, so that it is necessary to carefully separate blood platelets by preventing hemolysis from occuring.

SUMMARY OF THE INVENTION

It is the main object of the present invention to provide a filtering device having enhanced removal ratio of blood platelets.

Other objects and advantages of the present invention will become apparent from the following description.

Inventors of the present invention earnestly studied and discovered that blood platelets contained in blood is efficiently separated in a short time by using extremely fine polyester fiber having electro-microscopic rough surface. The present invention is made based on the above discovery.

In accordance with the present invention, there is provided a filtering device for blood platelets comprising polyester fibers having an average cross-sectional diameter of 0.1 to 5 μm, wherein there is formed electro-microscopic roughness on the surface of the polyester fibers. The rough surface of polyester fibers in the filtering device for blood platelet of the present invention is created by treating with a solvent having a solubility parameter of 8.0 to 12.5 [cal/ml]$^{\frac{1}{2}}$. The filtering device for blood platelets of the present invention has a filter wherein the mass of fibers is packed into a column so as for the mass of fibers to be characterised as possesing a bulk density of 0.1 to 0.6 g/cm³. The filtering device for blood platelets of the present invention has a filter wherein the mass of polyester fibers is packed into a column so as for the mass of fibers to satisfy the following relation:

$$\frac{1.38R}{8+R} < D < \frac{1.38R}{3+R}$$

where D is the bulk density [g/cm³] and R is the cross-sectional radius of polyester fiber [μm].

In accordance with the filtering device for blood platelets of the present invention, erythrocyte comes out from the outlet of the filter by changing the form thereof so as to pass through the space between fibers when blood is poured into the filtering device. On the other hand, leukocytes and blood platelets are caught by the fibers and spaces between fibers due to the repeated contact with the fibers. The filter of the filtering device of the present invention comprising fibers having surface with electro-microscopic roughness detected only by electro-microscope, so that blood platelets are caught by surface of the fibers and the separation efficiency is improved.

DETAILED DESCRIPTION

Figure 1:
FIG. 1 is a photograph of polyester fibers of the present invention taken by electro-microscope.

Referring now to the drawings for more complete understanding of the present invention, there is shown a filtering device for blood platelets.

Figure 2:
FIG. 2 is a photograph of fibers of comparative example taken by electro-microscope.
Figure 3A:
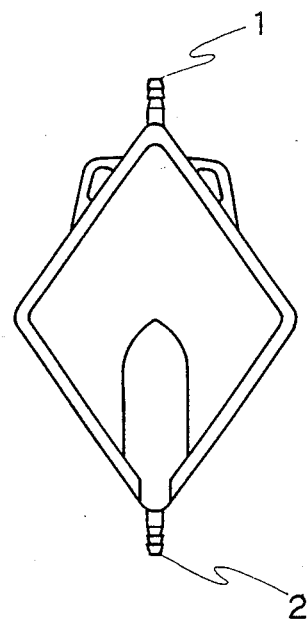
FIGS. 3A and 3B are plan view and side view of a column of an embodiment of the present invention respectively.
Figure 3B:
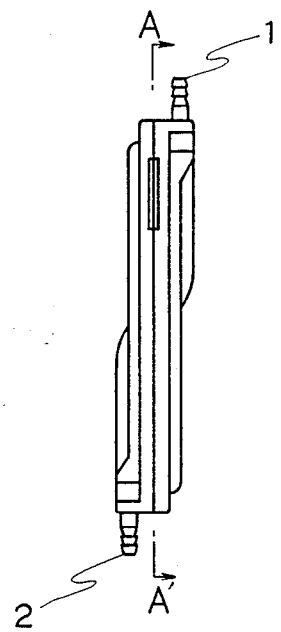
Figure 5A:
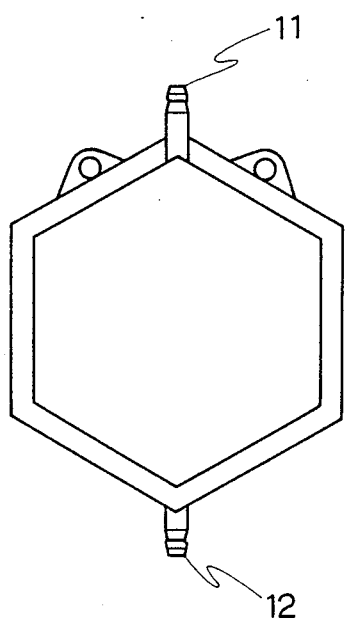
FIGS. 5A and 5B are plan view and side view of a column of another embodiment of the present invention respectively.
Figure 5B:
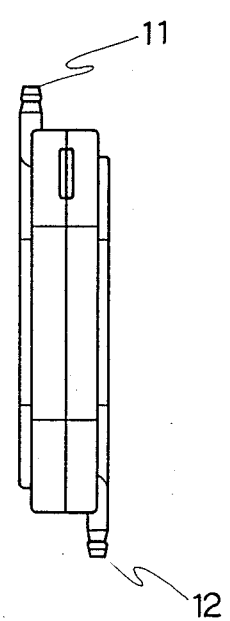
Figure 4:
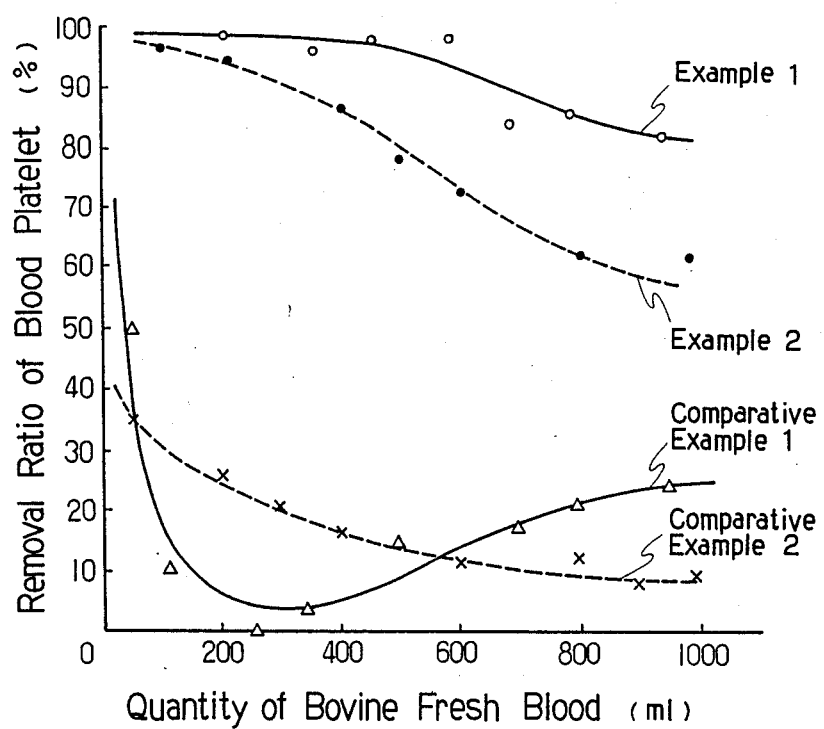
FIG. 4 is a graph showing the removal ratio of blood platelets upon quantity of bovine fresh blood for various kind of filters.
Figure 6:
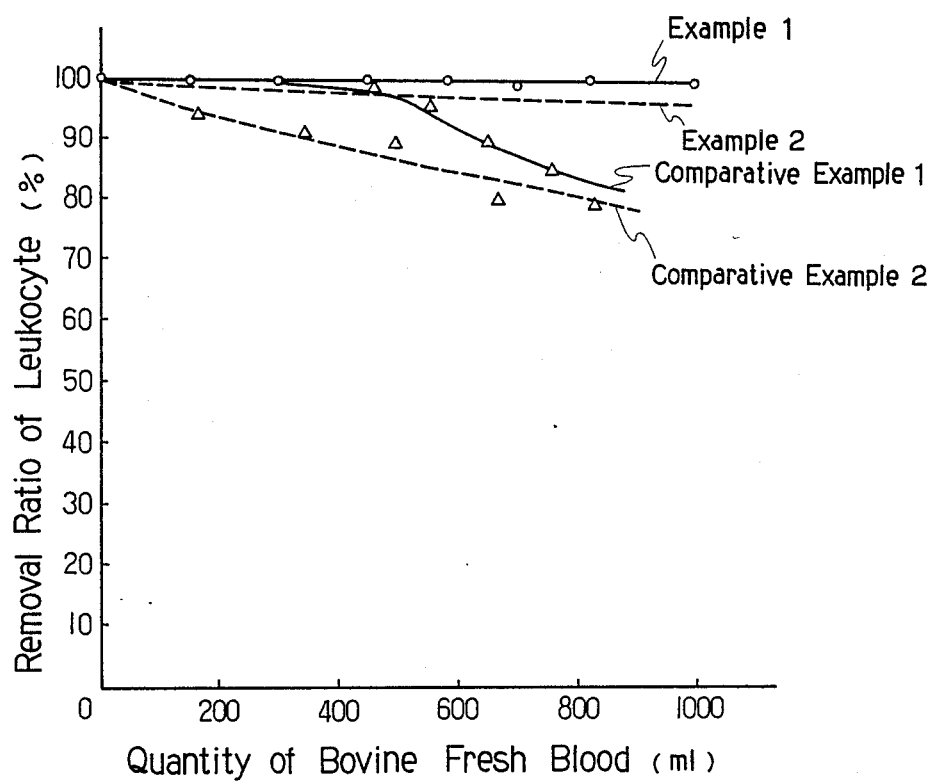
FIG. 6 is a graph showing the removal ratio of leukocytes upon quantity of bovine fresh blood for various kind of filters; and, FIG. 7 is a graph showing the removal ratio of blood platelets upon quantity of bovine fresh blood for various kind of filters.
Figure 7:
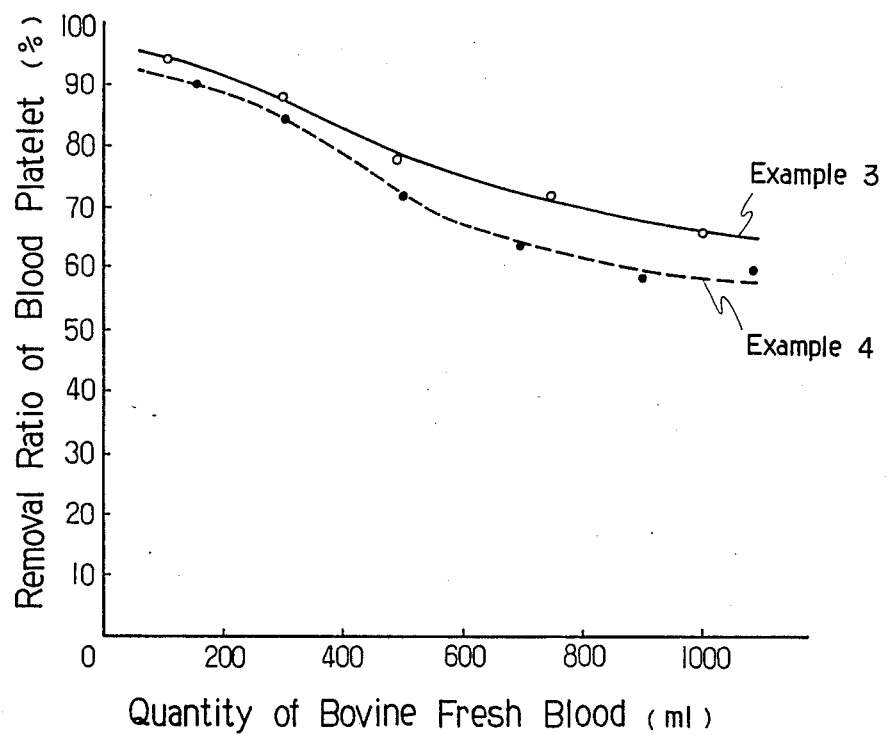

FIG. 1 is a photograph of polyester fibers of the present invention taken by electro-microscope;

FIG. 2 is a photograph of fibers of comparative example taken by electro-microscope;

FIGS. 3A and 3B are plan view and side view of a column of an embodiment of the present invention respectively;

FIG. 4 is a graph showing the removal ratio of blood platelets upon quantity of bovine fresh blood for various kind of filters;

FIGS. 5A and 5B are plan view and side view of a column of another embodiment of the present invention respectively;

FIG. 6 is a graph showing the removal ratio of leukocytes upon quantity of bovine fresh blood for various kind of filters; and, FIG. 7 is a graph showing the removal ratio of blood platelets upon quantity of bovine fresh blood for various kind of filters.

Polyester fibers used for a filtering device for blood platelets of the present invention comprising polyethylene telephthalate or its copolymer fiber of which the main component is ethylene terephthalate, wherein the average cross-sectional diameter of the fiber is 0.1 to 5 $\mu$m, preferably 0.5 to 3 $\mu$m. When the average cross-sectional diameter of the fiber becomes less than 0.1 $\mu$m, the strength of the fiber tends to be weak and it becomes difficult for them to be packed into a column. On the other hand, when the average cross-sectional diameter of the fiber becomes more than 5 $\mu$m, the removal ratio of blood platelets tends to be bad and the mass of fibers to be packed into column tends to be increased.

Electro-microscopic roughness is formed on the surface of the fibers. By the term "electro-microscopic roughness" herein is meant roughness which is detected not by an optical microscope having magnification of 1000 to 2000, but by an electro-microscope.

It is preferable that the surface of the fibers has concaves and convexes of 0.1 to 1 $\mu$m.

In order to form electro-microscopic roughness on the surface of fibers, it is preferable that the fibers are treated by solvent having a solubility parameter of 8.0 to 12.5 $[cal/ml]^{\frac{1}{2}}$. As solvents to be used here, dioxane, cyclohexane, xylene, cyclohexanone, acetic acid, cyclohexanol, ethyl lactate, toluene, benzene, methyl ethyl ketone, acetone, carbon tetrachloride, chlorobenzene, chloroform, methyl acetate, ethyl acetate, butyl acetate, methylene chloride are given for examples.

The treating of the fibers by solvent is carried out by dipping the fibers into solvent under the room temperature or suitably heating and/or under atomospheric pressure or elevated pressure. And then, the fibers are washed enough by solvent such as ethanol, methanol, trichloro-trifluoroethylene or water.

These fibers are packed into a column, and blood is poured into the column. During blood passes through the filter comprising the fibers, blood platelets are caught by the surface of the fibers and /or by the space between the fibers, i.e., the blood platelets are removed.

The fibers are packed into the column in the form of sheet or flocculent to make a filter. Alternately, the mass of the fibers, being sandwitched by blocks, bundles or sheets made of fibers having larger cross-sectional diameter, or by knitted or woven fabric, or by non-woven fabric, may be packed into the column to make a filter.

The blood platelets which are caught by the filter can be recovered by mechanical or chemical means.

It is preferable that a bulk density of the mass of fibers packed into the column is 0.1 to 0.6 g/cm$^3$. When the bulk density becomes less than 0.1 g/cm$^3$, the removal ratio of blood platelets tends to decrease. On the other hand, when the bulk density becomes more than 0.6 g/cm$^3$, hemolysis likely occurs due to destruction of blood corpuscle.

In order to increase the efficiency of the filter, in addition to the bulk density, the filter cross-sectional diameter must be taken into consideration. When the cross-sectional radius of fiber and the bulk density satisfy the following relation:

$$\frac{1.38R}{8 + R} < D < \frac{1.38R}{3 + R}$$

where D is the bulk density [g/cm$^3$] and R is the cross-sectional radius of fiber [$\mu$m], the filter displays its removal ability well without hemolysis. It is most suitable that the above relation is applied to the flow rate of blood under 100 ml/min.

EXAMPLE 1 AND COMPARATIVE EXAMPLE 1

Polyethylene terephthalate fibers, having an average cross-sectional diameter of 1.3 $\mu$m and length of 15 mm, were treated by being dipped into dioxane under temperature of 25° C for 30 minutes, and then, they were washed by ethanol and were dryed (hereinafter referred to as fiber(s) of Example 1). FIG. 1 is a photograph of the fibers of Example 1 taken by electro-microscope with magnification of 10,000.

On the other hand, FIG. 2 is a photograph of polyethylene terephthalate fibers without treatment by solvent (hereinafter referred to as fiber(s) of Comparative Example 1) was taken by electro-microscope with the same condition of the above.

From FIGS. 1 and 2, it is clearly understandable that electro-microscopic concaves and convexes were formed on the surface of the fibers of Example 1, and that no concaves and convexes were formed on the surface of the fibers of Comparative Example 1.

The fibers of Example 1 were formed into sheet, and then packed in a column shown in FIGS. 3A and 3B to make Main-filter.

As shown in Table 1, three layers were formed in the column, and the bulk density of the present embodiment (Example 1) of the present invention was 0.14 g/cm$^3$.

TABLE 1

|  | Fiber | Number of sheet(s) | Weight of sheet(s) (g) |
| --- | --- | --- | --- |
| Prefilter | SONTARA 8100 | 3 | 2.2 |
| Main-filter | fibers of Example 1 | 16 | 4.0 |
| End-filter | SONTARA 8100 | 1 | 0.7 |

(SONTARA 8100: non-woven fabric made by Du Pont)

Three layers were also formed in another column shown in FIGS. 3A and 3B by the same manner as the above, except that Main-filter comprises fibers of Comparative Example 1. The capacity of the column used were about 100 cm$^3$.

Blood is poured into the column from the inlet 1. During the blood passes through the filters packed into the column, blood platelets in the blood are caught by the filter. And then, the residual blood which is not caught by the filter comes out from outlet 2.

The column has hinged part so that it can be opened for packing the layers of filters into the column, and that can be shut along the line A—A' of FIG. 3B.

Next, bovine fresh blood was continuously poured into the columns from the inlet 1 at the rate of 40 ml/min under 25° C. The removal ratio of blood platelets against quantity of bovine fresh blood was measured. The result is shown in FIG. 4. Further, the removal ratio of leukocytes was measured. The result is shown in FIG. 6.

From FIG. 4, it is clearly understandable that the filtering device of Example 1 of the present invention can almost entirely remove the blood platelets up to 500 ml of treating blood, and that the filtering device of Comparative Example 1 of which fibers for Main-filter is not treated by solvent cannot remove the blood platelets well.

In FIG. 4, that the removal ratio of blood platelets of Comparative Example 1 is about 50 % at the initial stage means that the blood platelets are caught by the space between the fibers.

Further, from FIG. 6, it is understandable that the removal ratio of leukocytes of the filtering device of Example 1 of the present invention is almost 100% up to 1000 ml of treating blood, and that the removal ratio of leukocytes of the filtering device of Comparative Example 1 is on the decrease from near 500 ml of treating blood.

EXAMPLE 2

Polyethylene terephthalate fibers, having an average cross-sectional diameter of 2.3 $\mu$m and length of 15 mm, were treated by being dipped into methyl ethyl ketone under temperature of 35° C. for an hour, and then, they were washed by ethanol and were dried (hereinafter referred to as fiber(s) of Example 2). It was observed by electro-microscope that electro-microscopic concaves and convexes were formed on the surface of the fibers of Example 2.

Then, the fibers of Example 2 were formed into sheets and packed into the column shown in FIGS. 3A and 3B to make Main-filter.

The construction of the filtering device was the same one as Example 1 except for the material and the number of sheets of Main-filter and the bulk density. The nmber of sheets of Main-filter of Example 2 was nine, and the bulk density was 0.18 g/cm$^3$.

Bovine fresh blood was poured into column by the same manner as described in Example 1. The removal ratio of blood platelets and leukocytes were measured. The results are shown in FIGS. 4 and 6 respectively. The removal ratio of blood platelets of the filtering device of Example 2 is lower than that of Example 1. However, the device is applicable enough to separation of blood platelets.

And also, the removal ratio of leukocytes of Example 2 is a little lower than that of Example 1. However, the device is applicable enough to separation of leukocytes.

COMPARATIVE EXAMPLE 2

Polyethylene terephthalate fibers, having an average cross-sectional diameter of 6.1 $\mu$m and length of 15 mm, were treated by being dipped into dioxane under temperature of 25° C. for 30 minutes, and then, they were washed by ethanol and were dried (hereinafter referred to as fiber(s) of Comparative Example 2). It was observed by electro-microscope that electro-microscopic concaves and convexes were formed on the surface of the fibers of Comparative Example 2.

Then, the fibers of Comparative Example 2 were formed into sheets and packed into the column shown FIGS. 3A and 3B to make Main-filter.

The construction of the filtering device was the same one as Example 2 except for the material of sheets of Main-filter, and the bulk density. The number of sheets of Main-filter of Comparative Example 2 is nine.

Bovine fresh blood was poured into the column by the same manner as described in Example 1. The removal ratio of blood platelets and leukocytes were measured. The results are shown in FIGS. 4 and 6. The removal ratio of blood platelet of Comparative Example 2 is very low as compared with those of Examples of the present invention. The removal ratio of leukocytes is rather low as compared with those of Examples of the present invention.

EXAMPLE 3

Polyethylene terephthalate fibers, having an average cross-sectional diameter of 3.1 $\mu$m and length of 15 mm, were treated by being dipped into mixture of dioxane and water (mixing ratio of weight is 1:1) in an autoclave for an hour, and then, they were washed and were dryed (hereinafter referred to as fiber(s) of Example 3). It was observed by electro-microscope that electro-microscopic concaves and convexes were formed on the surface of the fibers of Example 3.

Then, the fibers of Example 3 were packed into a column shown in FIGS. 5A and 5B to make Main-filter.

The filter comprises three layers, i.e., Prefilter, Main-filter and End-filter. Prefilter and Endfilter were made SONTARA 8100 shown in Table 1, and the weight of Prefilter and End-filter were equal to those of Example 1 shown in Table 1. The weight of Mainfilter was 11.2 g and the bulk density was 0.30 g/cm$^3$.

For the column shown in FIGS. 5A and 5B, blood is poured into the column from inlet 11, passes through the filters packed into the column, and comes out from outlet 12.

Bovine fresh blood was poured into the column at the rate of 46 ml/min under the temperature of 25° C. And then, the removal ratio of blood platelets was measured. The result is shown in FIG. 7.

EXAMPLE 4

Polyethylene terephthalate fibers, having an average cross-sectional diameter of 5.0 $\mu$m and length of 15 mm, were treated by the same way of Example 3, i.e., be being dipped into mixture of dioxane and water in an autoclave (hereinafter referred to as fiber(s) of Example 4). It was observed by electro-microscope that electro-microscopic concaves and convexes were formed on the surface of the fibers of Example 4.

Then, the fibers of Example 4 were packed into a column shown in FIGS. 5A and 5B to make Main-filter. The weight of packed fibers was 15.2 g, and the bulk density was 0.41 g/cm$^3$. The same Prefilter and End-filter as Example 3 were adopted for Prefilter and End-filter.

Bovine fresh blood was poured into the column at the rate of 46 ml/min under the temperature of 25° C., i.e., the same condition as Example 3. And then, the removal ratio of blood platelets was measured. The result is shown in FIG. 7.

From FIG. 7, it is clearly understandable that the removal ratio of blood platelets of the filtering device of Example 4, having a larger average diameter of fiber, is lower than that of Example 3, having a smaller average diameter of fiber.

EXAMPLES 5 TO 10, AND COMPARATIVE EXAMPLES 3 TO 10

Fibers, which were used in Examples 1 to 4 for Main-filter, were packed into the columns shown in FIGS. 5A and 5B to make Examples 5 to 10 and Comparative Examples 3 to 10. The average cross-sectional diameters and the bulk densities were settled as shown in Table 2.

Bovine fresh blood was poured into the column at the rate of 45 ml/min. And then, the removal ratio of blood platelets was measured and the existence of hemolysis was checked. The results are shown in Table 2.

TABLE 2

| | Fiber diameter (μm) | Bulk density (g/cm³) | Removal ratio of blood platelet (%) | Hemolysis existence |
|---|---|---|---|---|
| Example 5 | 1.3 | 0.18 | 98 | O |
| Example 6 | 2.3 | 0.22 | 91 | O |
| Example 7 | 3.5 | 0.40 | 85 | O |
| Example 8 | 3.5 | 0.25 | 77 | O |
| Example 9 | 4.8 | 0.33 | 70 | O |
| Example 10 | 4.8 | 0.52 | 81 | O |
| Comparative Example 3 | 1.3 | 0.08 | 30 | O |
| Comparative Example 4 | 1.3 | 0.26 | 98 | X |
| Comparative Example 5 | 2.3 | 0.15 | 41 | O |
| Comparative Example 6 | 2.3 | 0.40 | 89 | X |
| Comparative Example 7 | 3.5 | 0.20 | 34 | O |
| Comparative Example 8 | 3.5 | 0.52 | 81 | X |
| Comparative Example 9 | 4.8 | 0.27 | 27 | O |
| Comparative Example 10 | 4.8 | 0.65 | 70 | X | where
O: not existence
X: existence

In Table 2, removal ratio of blood platelets is a value in treating 500 ml of bovine fresh blood.

Checking of the existence of hemolysis was carried out by visually comparing color difference between plasma separated from blood before and after filtering by centrifugal separation.

From Table 2, it is clearly understandable that there is a tendency that the larger the average crosssectional diameter becomes, the heavier the preferable bulk density becomes.

According to the present invention, as described hereinabove, there can be realized a filtering device for blood platelets having a simple construction, wherein blood platelets are caught efficiently and the removal of blood platelets are carried out in a short time. Consequently, the filtering device for blood platelets of the present invention is the most suitable for the removal of blood platelets at operation.

It should also be understood that the foregoing relates to only the scope of the invention is defined by the appended claims rather than by the description preceding them, and all changes that fall within meets and founds of the claims or equivalence of such meets and bounds are therefore intended to embraced by the claims.

What we claim is:

1. A filtering device for blood platelets comprising a column packed with polyester fibers having an average cross-sectional diameter of 0.1~5 μm, a bulk density of from 0.1~0.6 g/cm³, and wherein the surface of said fibers have roughness of about 0.1 to 1.0 μm which is detectable by an electro-microscope which roughness has been formed by treating the fibers with solvent having a solubility parameter of 8.0~12.5 cal/ml$^{0.5}$.

2. A filtering device for blood platelets as claimed in claim 1 wherein said solvent is at least one of the solvents selected from the group consisting of dioxane, cyclohexane, xylene, cyclohexanone, acetic acid, toluene, cyclohexanol, ethyl lactate, benzene, methyl ethyl ketone, acetone, carbon tetrachloride, chlorobenzene, chloroform, methyl acetate, ethyl acetate, butyl acetate, methylene chloride.

3. A filtering device for blood platelets as claimed in claim 1 wherein the cross-sectional radius of the fibers and the bulk density thereof in said column satisfy the following relation:

$$\frac{1.38R}{8 + R} < D < \frac{1.38R}{3 + R}$$

where D is the bulk density in g/cm³ and R is the cross-sectional radius of the fibers in μm.

* * * * *